United States Patent
Matwiejuk et al.

(10) Patent No.: US 11,267,839 B2
(45) Date of Patent: Mar. 8, 2022

(54) CRYSTALLINE FORMS OF LNT

(71) Applicant: GLYCOM A/S, Hørsholm (DK)

(72) Inventors: Martin Matwiejuk, Hamburg (DE);
Pierre Chassagne, Beaumont (FR);
Markus Jondelius Hederos, Trelleborg (SE)

(73) Assignee: GLYCOM A/S, Hørsholm (DK)

(*) Notice: Subject to any disclaimer, the term of this patent is extended or adjusted under 35 U.S.C. 154(b) by 0 days.

(21) Appl. No.: 16/913,656

(22) Filed: Jun. 26, 2020

(65) Prior Publication Data

US 2020/0325166 A1   Oct. 15, 2020

Related U.S. Application Data

(62) Division of application No. 16/063,367, filed as application No. PCT/DK2016/050441 on Dec. 16, 2016, now Pat. No. 10,696,705.

(30) Foreign Application Priority Data

Dec. 17, 2015  (DK) .......................... PA 2015 70832
Oct. 31, 2016  (DK) .......................... PA 2016 70856

(51) Int. Cl.
  C07H 1/06   (2006.01)
  C07H 13/04  (2006.01)
  A61K 31/702 (2006.01)
  A23L 33/125 (2016.01)
  A23L 33/00  (2016.01)

(52) U.S. Cl.
  CPC .............. *C07H 1/06* (2013.01); *A23L 33/125* (2016.08); *A23L 33/40* (2016.08); *A61K 31/702* (2013.01); *C07H 13/04* (2013.01); *A23V 2002/00* (2013.01); *C07B 2200/03* (2013.01)

(58) Field of Classification Search
  None
  See application file for complete search history.

(56) References Cited

FOREIGN PATENT DOCUMENTS

EP   1405856 A1    4/2004
WO   2014086373 A1 6/2014

OTHER PUBLICATIONS

Takamura, T., et al., "Chemical Modification of Lactose. XIII. Synthesis of Lacto-N-tetraose," Chem. Pharm. Bull., 1980, vol. 28(6), pp. 1804-1809.
Takamura, T. et al., "Chemical Modification of Lactose. XIII Synthesis of Lacto-N-tetraose," Chem. Pharm. Bull., 1979, vol. 27(6), pp. 1497-1499.
Malpress, F.H., et al., "The Oligosaccharides of Human Milk," Biochem. J., 1958, vol. 68(4), pp. 708-717.
Kuhn et al., "About an N-containing tetrasaccharide from mother's milk," Chemische Berichte, 1953, vol. 86, pp. 627-830.

*Primary Examiner* — Layla D Berry
(74) *Attorney, Agent, or Firm* — Neal, Gerber & Eisenberg LLP

(57) ABSTRACT

The invention relates to crystalline polymorphs of lacto-N-tetraose (LNT) and methods for making the same for use in pharmaceutical compositions, nutritional formulations and food supplements.

5 Claims, 4 Drawing Sheets

CRYSTALLINE FORMS OF LNT

CROSS-REFERENCE TO RELATED APPLICATION

This application is a divisional application of U.S. application Ser. No. 16/063,367, filed Jun. 18, 2018, which is a national stage entry pursuant to 35 U.S.C. § 371 of International Application No. PCT/DK2016/050441, filed on Dec. 16, 2016, which claims priority to Denmark Patent Application No. PA 2015 70832, filed on Dec. 17, 2015, and Denmark Patent Application No. PA 2016 70856, filed Oct. 31, 2016, the contents of all of which are fully incorporated herein by reference.

FIELD OF THE INVENTION

The present invention provides crystalline modifications of Galpβ1-3GlcNAcpβ1-3Galpβ1-4Glc (lacto-N-tetraose, LNT), a method of making them and formulations containing the same.

BACKGROUND OF THE INVENTION

The human milk oligosaccharide LNT has previously been crystallized. Kuhn et al. [*Chem. Ber.* 86, 827, (1953)] isolated LNT from mother's milk for the first time and crystallized it from aqueous ethanol. Upon drying, the air-dried crystalline material lost more than 10% of its weight (melting point 200-205° C. (dec.)), but its crystal structure did not change according to X-ray power diffraction measurements. The so-dried material proved to be hygroscopic as it took back around 8% of its weight when stored in air. Later, the same authors reported the obtention of crystalline LNT by partial hydrolysis of lacto-N-fucopentaose I [*Chem. Ber.* 89, 2514 (1956)] or sialylated LNT [*Chem. Ber.* 95, 513 (1962)], both isolated from mother's milk, followed by crystallization; their reported decomposition points were 205±10° C. ("depending on water content and the speed of heating") and 211-214° C., respectively; both samples were considered to be identical with the previously reported one based on their X-ray power diffractogram and/or IR spectrum. Similarly, Malpress et al. [*Biochem. J.* 68, 708 (1958)]isolated LNT from mother's milk having a melting point of 204-205° C. Takamura et al. [*Chem. Pharm. Bull.* 27, 1497 (1979) and ibid. 28, 1804 (1980)] reported a melting point of 225-228° C. for LNT made by chemical total synthesis and crystallized from aqueous ethanol.

Crystallization or recrystallization is one of the simplest and cheapest methods to separate a product from contaminants and obtain a pure substance. Providing alternative crystalline forms of a solid compound is an important aspect of the product's development, because the different crystalline forms affect the compound's properties—for example, thermodynamic stability, solubility, density, hygroscopicity, electrical properties (such as dielectric constant, conductivity), mechanical properties (such as friability, hardness, breaking strength, elasticity), optical properties (such as colour, transparency, refraction), etc.—diversely. Polymorphs or other crystalline forms provide alternative means for improving a product's characteristics and usefulness.

For this reason, ways have been sought for obtaining other crystalline forms of LNT which have different, preferably advantageous, physical properties (such as e.g. hygroscopicity, stability, dissolution rate, purity, filterability, drying properties, flowability of the powder, etc.) for facilitating its isolation from a complex milieu or its use in pharmaceutical or nutritional compositions.

Short Description of the Invention

The present invention provides novel crystalline polymorphs of LNT, methods for making the novel crystalline polymorphs of LNT that can be produced in large scale. Thus, the crystalline products of this invention are each a high purity LNT that are suitable for nutritional and pharmaceutical products.

BRIEF DESCRIPTION OF THE FIGURES

The invention will be described in further detail hereinafter with reference to the accompanying figures, in which.

DETAILED DESCRIPTION OF THE INVENTION

This invention provides a first LNT crystalline form A. The crystalline LNT form A comprises X-ray powder diffraction reflections, based on a measurement using CuKα radiation, at 19.21±0.2 2Θ angle, preferably at 19.21 and 4.20±0.2 2Θ angles, more preferably at 19.21, 4.20 and 19.99±0.2 2Θ angles, yet more preferably at 19.21, 4.20, 19.99 and 20.63±0.2 2Θ angles, even more preferably at 19.21, 4.20, 19.99, 20.63 and 18.80±0.2 2Θ angles, even more preferably at 19.21, 4.20, 19.99, 20.63, 18.80 and 19.82±0.2 2Θ angles, even more preferably at 19.21, 4.20, 19.99, 20.63, 18.80, 19.82 and 8.60±0.2 2Θ angles, even more preferably at 19.21, 4.20, 19.99, 20.63, 18.80, 19.82, 8.60 and 6.52±0.2 2Θ angles, most preferably at 19.21, 4.20, 19.99, 20.63, 18.80, 19.82, 8.60, 6.52 and 20.47±0.2 2Θ angles, particularly at 19.21, 4.20, 19.99, 20.63, 18.80, 19.82, 8.60, 6.52, 20.47 and 21.96±0.2 2Θ angles.

In one embodiment, the crystalline LNT form A comprises X-ray powder diffraction reflections, based on a measurement using CuKα radiation, at 19.21±0.1 2Θ angle, preferably at 19.21 and 4.20±0.1 2Θ angles, more preferably at 19.21, 4.20 and 19.99±0.1 2Θ angles, yet more preferably at 19.21, 4.20, 19.99 and 20.63±0.1 2Θ angles, even more preferably at 19.21, 4.20, 19.99, 20.63 and 18.80±0.1 2Θ angles, even more preferably at 19.21, 4.20, 19.99, 20.63, 18.80 and 19.82±0.1 2Θ angles, even more preferably at 19.21, 4.20, 19.99, 20.63, 18.80, 19.82 and 8.60±0.1 2Θ angles, even more preferably at 19.21, 4.20, 19.99, 20.63, 18.80, 19.82, 8.60 and 6.52±0.1 2Θ angles, most preferably at 19.21, 4.20, 19.99, 20.63, 18.80, 19.82, 8.60, 6.52 and 20.47±0.1 2Θ angles, particularly at 19.21, 4.20, 19.99, 20.63, 18.80, 19.82, 8.60, 6.52, 20.47 and 21.96±0.1 2Θ angles.

Figure 1:
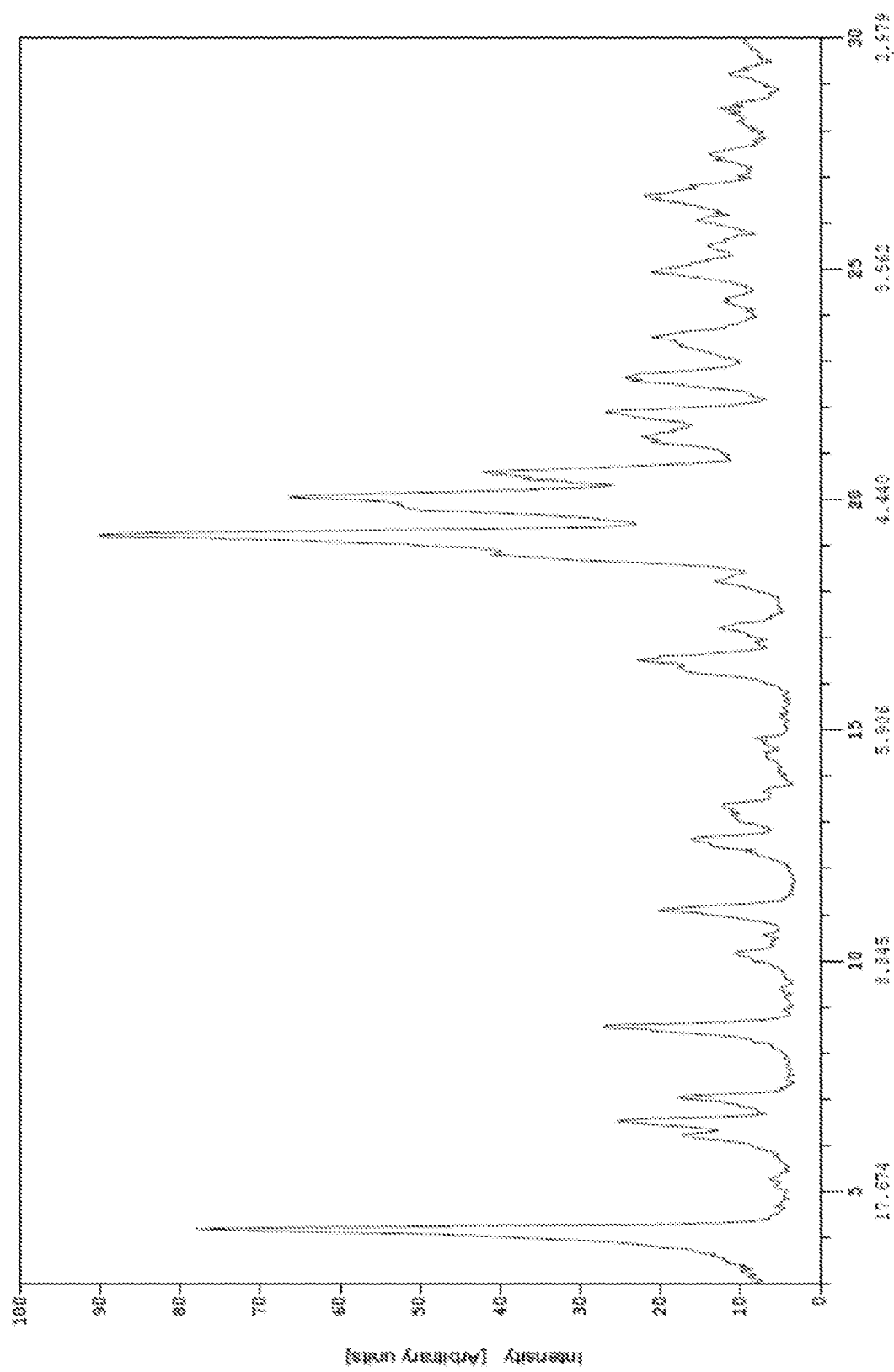
FIG. 1 shows the X-ray powder diffraction pattern of the crystalline LNT form A.

In other embodiment, the crystalline LNT form A has an X-ray powder diffraction diagram as shown in FIG. 1.

List of peaks of the XRPD pattern of the crystalline LNT form A is reported in Table 1.

TABLE 1

| 2Θ | rel. intensity |
|---|---|
| 4.20 | 80 |
| 6.22 | 15 |
| 6.52 | 25 |
| 7.04 | 16 |
| 8.60 | 25 |
| 10.14 | 8 |
| 10.61 | 4 |
| 11.11 | 18 |
| 12.47 | 5 |
| 12.62 | 12 |
| 13.09 | 8 |
| 13.32 | 5 |
| 13.40 | 5 |
| 13.68 | 4 |
| 14.38 | 3 |
| 14.80 | 5 |
| 16.34 | 10 |
| 16.52 | 22 |
| 17.21 | 10 |
| 18.26 | 11 |
| 18.80 | 43 |
| 19.21 | 100 |
| 19.76 | 20 |
| 19.82 | 30 |
| 19.99 | 55 |
| 20.16 | 20 |
| 20.35 | 10 |
| 20.47 | 25 |
| 20.63 | 45 |
| 21.32 | 20 |
| 21.96 | 25 |

LNT crystalline form A has a capillary melting point of 226-231° C. The conventionally dried sample (in desiccator over $P_2O_5$) has a water content of 12.5-13.0 wt %. In TG-DSC measurement a weight loss of about 5.3 wt % is observed between 35 and 120° C.

This invention also provides a second LNT crystalline form B. The crystalline LNT form B comprises X-ray powder diffraction reflections, based on a measurement using CuKα radiation, at 19.25±0.2 2Θ angle, preferably at 19.25 and 9.19±0.2 2Θ angles, more preferably at 19.25, 9.19 and 6.88±0.2 2Θ angles, yet more preferably at 19.25, 9.19, 6.88 and 21.07±0.2 2Θ angles, even more preferably at 19.25, 9.19, 6.88, 21.07 and 20.87±0.2 2Θ angles, even more preferably at 19.25, 9.19, 6.88, 21.07, 20.87 and 19.94±0.2 2Θ angles, even more preferably at 19.25, 9.19, 6.88, 21.07, 20.87, 19.94 and 19.66±0.2 20 angles, even more preferably at 19.25, 9.19, 6.88, 21.07, 20.87, 19.94, 19.66 and 6.02±0.2 2Θ angles, most preferably at 19.25, 9.19, 6.88, 21.07, 20.87, 19.94, 19.66, 6.02 and 22.30±0.2 2Θ angles, particularly at 19.25, 9.19, 6.88, 21.07, 20.87, 19.94, 19.66, 6.02, 22.30 and 25.15±0.2 2Θ angles.

In one embodiment, the crystalline LNT form B comprises X-ray powder diffraction reflections, based on a measurement using CuKα radiation, at 19.25±0.1 2Θ angle, preferably at 19.25 and 9.19±0.1 2Θ angles, more preferably at 19.25, 9.19 and 6.88±0.1 2Θ angles, yet more preferably at 19.25, 9.19, 6.88 and 21.07±0.1 2Θ angles, even more preferably at 19.25, 9.19, 6.88, 21.07 and 20.87±0.1 2Θ angles, even more preferably at 19.25, 9.19, 6.88, 21.07, 20.87 and 19.94±0.1 2Θ angles, even more preferably at 19.25, 9.19, 6.88, 21.07, 20.87, 19.94 and 19.66±0.1 2Θ angles, even more preferably at 19.25, 9.19, 6.88, 21.07, 20.87, 19.94, 19.66 and 6.02±0.1 2Θ angles, most preferably at 19.25, 9.19, 6.88, 21.07, 20.87, 19.94, 19.66, 6.02 and 22.30±0.1 2Θ angles, particularly at 19.25, 9.19, 6.88, 21.07, 20.87, 19.94, 19.66, 6.02, 22.30 and 25.15±0.1 2Θ angles.

Figure 2:
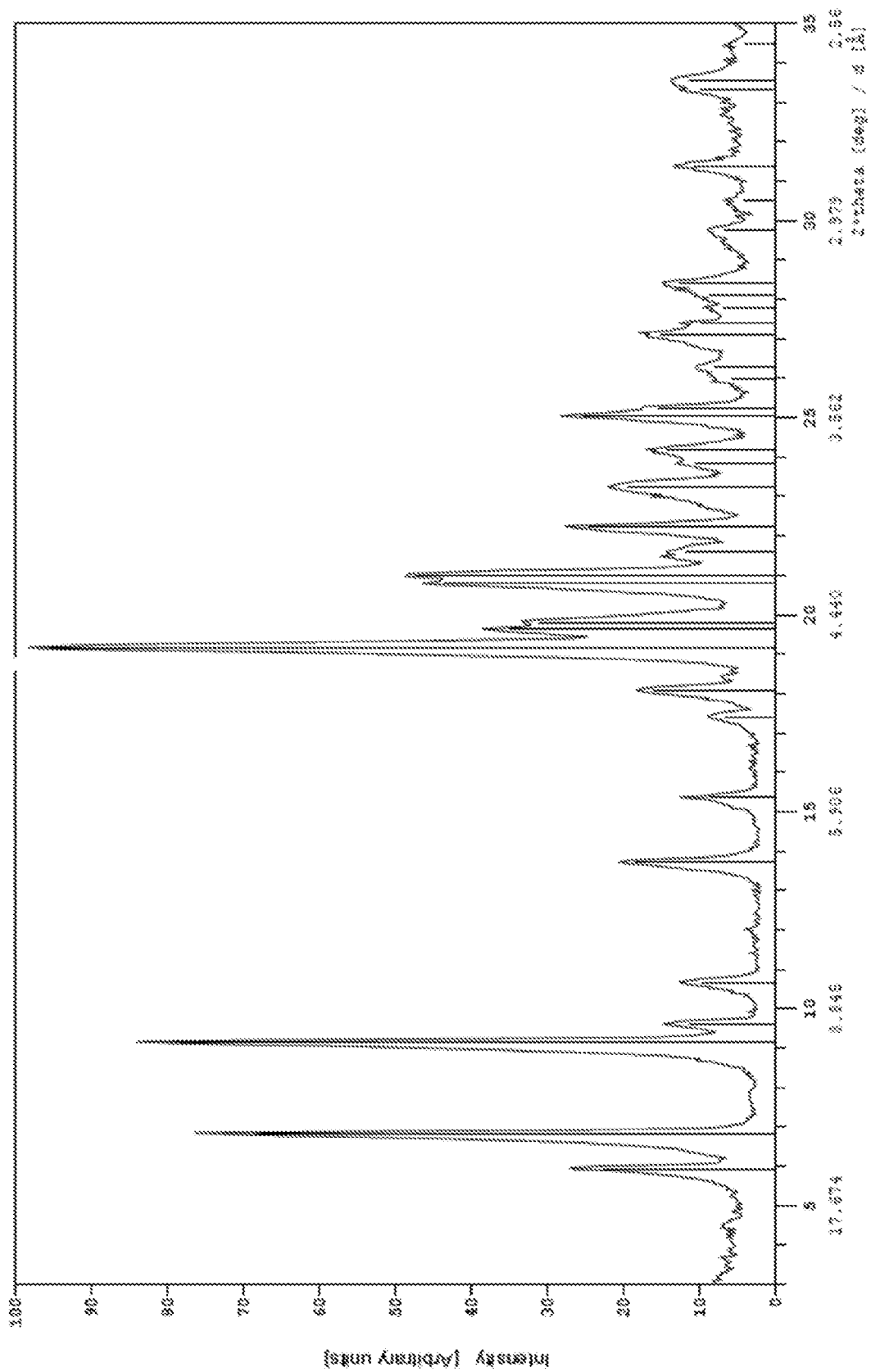
FIG. 2 shows the X-ray powder diffraction pattern of the crystalline LNT form B.

In other embodiment, the crystalline LNT form B has an X-ray powder diffraction diagram as shown in FIG. 2.

List of peaks of the XRPD pattern of the crystalline LNT form A is reported in Table 2.

TABLE 2

| 2Θ | rel. intensity |
|---|---|
| 6.02 | 25 |
| 6.88 | 78 |
| 9.10 | 10 |
| 9.19 | 80 |
| 9.63 | 3 |
| 9.70 | 10 |
| 10.73 | 12 |
| 12.05 | 1 |
| 13.78 | 18 |
| 15.43 | 8 |
| 17.49 | 3.5 |
| 17.55 | 4 |
| 18.11 | 13 |
| 18.40 | 5 |
| 19.25 | 100 |
| 19.26 | 1 |
| 19.66 | 25 |
| 19.94 | 31 |
| 20.83 | 1 |
| 20.87 | 35 |
| 21.07 | 40 |
| 21.55 | 8 |
| 21.67 | 10 |
| 22.30 | 22 |
| 22.95 | 8 |
| 23.30 | 19 |
| 23.40 | 15 |
| 23.94 | 6 |
| 24.12 | 5 |
| 24.23 | 13 |
| 25.15 | 19 |
| 25.29 | 15 |
| 26.15 | 3.5 |
| 26.35 | 6.5 |
| 27.12 | 13 |
| 27.29 | 9 |
| 27.52 | 8 |
| 28.06 | 5 |
| 28.11 | 10 |
| 28.50 | 11 |
| 28.68 | 6 |

LNT crystalline form B has a capillary melting point 239-243° C. The air dried sample has a water content of 8.9-9.2 wt %.

This invention also provides a third LNT crystalline form C. The crystalline LNT form C comprises X-ray powder diffraction reflections, based on a measurement using CuKα radiation, at 20.22±0.2 2Θ angle, preferably at 20.22 and 9.36±0.2 2Θ angles, more preferably at 20.22, 9.36 and 19.80±0.2 2Θ angles, yet more preferably at 20.22, 9.36, 19.80 and 20.47±0.2 2Θ angles, even more preferably at 20.22, 9.36, 19.80, 20.47 and 4.67±0.2 2Θ angles, even more preferably at 20.22, 9.36, 19.80, 20.47, 4.67 and 18.79±0.2 2Θ angles, even more preferably at 20.22, 9.36, 19.80, 20.47, 4.67, 18.79 and 6.82±0.2 2Θ angles, even more preferably at 20.22, 9.36, 19.80, 20.47, 4.67, 18.79, 6.82 and 21.82±0.2 2Θ angles, even more preferably at 20.22, 9.36, 19.80, 20.47, 4.67, 18.79, 6.82, 21.82 and 7.93±0.2 2Θ angles, most preferably at 20.22, 9.36, 19.80, 20.47, 4.67, 18.79, 6.82, 21.82, 7.93 and 19.16±0.2 2Θ angles, particularly 20.22, 9.36, 19.80, 20.47, 4.67, 18.79, 6.82, 21.82, 7.93, 19.16 and 19.45±0.2 2Θ angles.

In one embodiment, the crystalline LNT form C comprises X-ray powder diffraction reflections, based on a measurement using CuKα radiation, at 20.22±0.1 2Θ angle, preferably at 20.22 and 9.36±0.1 2Θ angles, more preferably at 20.22, 9.36 and 19.80±0.1 2Θ angles, yet more preferably at 20.22, 9.36, 19.80 and 20.47±0.1 2Θ angles, even more preferably at 20.22, 9.36, 19.80, 20.47 and 4.67±0.1 2Θ angles, even more preferably at 20.22, 9.36, 19.80, 20.47, 4.67 and 18.79±0.1 2Θ angles, even more preferably at 20.22, 9.36, 19.80, 20.47, 4.67, 18.79 and 6.82±0.1 2Θ angles, even more preferably at 20.22, 9.36, 19.80, 20.47, 4.67, 18.79, 6.82 and 21.82±0.1 2Θ angles, even more preferably at 20.22, 9.36, 19.80, 20.47, 4.67, 18.79, 6.82, 21.82 and 7.93±0.1 2Θ angles, most preferably at 20.22, 9.36, 19.80, 20.47, 4.67, 18.79, 6.82, 21.82, 7.93 and 19.16±0.1 2Θ angles, particularly 20.22, 9.36, 19.80, 20.47, 4.67, 18.79, 6.82, 21.82, 7.93, 19.16 and 19.45±0.1 2Θ angles.

Figure 3:
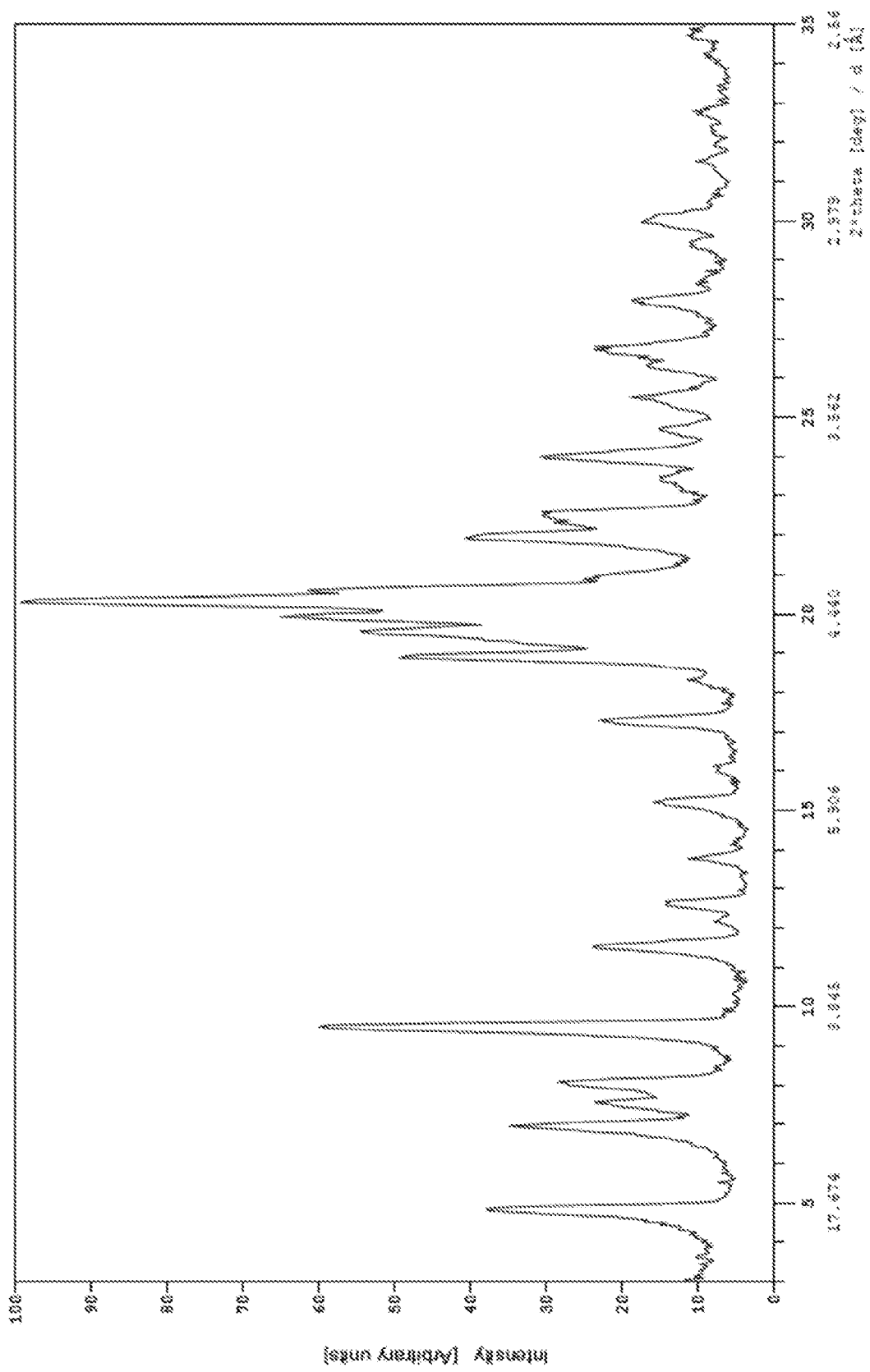
FIG. 3 shows the X-ray powder diffraction pattern of the crystalline LNT form C.

In other embodiment, the crystalline LNT form C has an X-ray powder diffraction diagram as shown in FIG. 3.

List of peaks of the XRPD pattern of the crystalline LNT form C is reported in Table 3.

TABLE 3

| 2Θ | rel. intensity |
|---|---|
| 4.67 | 50 |
| 6.82 | 42 |
| 7.39 | 25 |
| 7.93 | 32 |
| 9.36 | 75 |
| 11.35 | 10 |
| 11.46 | 16 |
| 12.06 | 4 |
| 12.49 | 15 |
| 13.66 | 8 |
| 14.83 | 5 |
| 15.09 | 15 |
| 15.89 | 4 |
| 17.15 | 21 |
| 18.18 | 7 |
| 18.79 | 48 |
| 19.16 | 30 |
| 19.42 | 20 |
| 19.45 | 30 |
| 19.80 | 55 |
| 20.01 | 5 |
| 20.22 | 100 |
| 20.47 | 52 |
| 20.84 | 15 |
| 21.82 | 34 |
| 21.85 | 10 |
| 22.20 | 20 |
| 22.45 | 25 |
| 23.07 | 4 |
| 23.36 | 7 |
| 23.83 | 8 |
| 23.85 | 15 |
| 23.93 | 10 |
| 24.53 | 4 |
| 24.60 | 3 |
| 24.72 | 3 |
| 25.14 | 6 |
| 25.38 | 11 |
| 25.45 | 6 |

TABLE 3-continued

| 2Θ | rel. intensity |
|---|---|
| 26.10 | 5 |
| 26.54 | 10 |
| 26.620 | 5 |
| 26.71 | 15 |
| 27.80 | 10 |

LNT crystalline form C has a capillary melting point 249-255° C. The air dried sample has a water content of 6.4-9.4 wt %. Indexing of the XRPD diagram of form C results in the following cell parameters:

| symmetry | space group | cell parameters | | | | | | cell volume |
|---|---|---|---|---|---|---|---|---|
| | | a | b | c | α | β | γ | |
| orthorhombic | P212121 | 23.93 Å | 30.85 Å | 4.778 Å | 90 | 90 | 90 | 3527.6 Å³ |

In one embodiment, LNT crystalline form C can be prepared in the following way: LNT is dissolved in around 2.5-3.5 volumes of water and heated to around 55-65° C. Methanol (around 6-7.5 volumes) is then slowly added to aqueous solution. The so-obtained solution is stirred at the same temperature until spontaneous nucleation, then the suspension is slowly cooled to 0-25° C. and the crystals of LNT polymorph C are separated by filtration.

Alternatively, a 20-25 w/v % LNT solution in water is heated to around 30-40° C. to which, under stirring, methanol is added in two steps: a) first around 4-5 volumes of methanol to give a clear solution, then b) the same volumes of methanol in portions, preferably in around 0.6-0.85 volumes portions, to give a suspension. In some embodiments, preferably, between step a) and b) seeding crystals of LNT polymorph C can be added. After completion of the methanol addition the suspension is stirred between 30-60° C. for a couple of hours, then slowly cooled to 0-25° C. and the crystals of LNT pdymorph C are separated by filtration.

In the above crystallization methods, the term "around" means a deviation from the indicated value by 5-10%; and the term "volume" means that how many ml of solvent is added to 1 g of LNT.

After LNT form C is crystallized (by any means), the crystals can be dried in vacuum for less than one day, typically less than 21 hours at 30-50 mbar and at not more than 50-60° C. In case of drying at atmospheric pressure, the temperature can be as high as 70° C., but the drying time preferably does not exceed 5 hours. At lower temperature proportionally longer drying time can be applied.

This invention also provides a fourth LNT crystalline form D. The crystalline LNT form D comprises X-ray powder diffraction reflections, based on a measurement using CuKα radiation, at 19.17±0.2 2Θ angle, preferably at 19.17 and 20.91±0.2 2Θ angles, more preferably at 19.17, 20.91 and 10.67±0.2 2Θ angles, yet more preferably at 19.17, 20.91, 10.67 and 15.90±0.2 2Θ angles, even more preferably at 19.17, 20.91, 10.67, 15.90 and 9.32±0.2 2Θ angles, even more preferably at 19.17, 20.91, 10.67, 15.90, 9.32 and 21.16±0.2 2Θ angles, even more preferably at 19.17, 20.91, 10.67, 15.90, 9.32, 21.16 and 23.44±0.2 2Θ angles, even more preferably at 19.17, 20.91, 10.67, 15.90, 9.32, 21.16, 23.44 and 21.40±0.2 2Θ angles, even more preferably at 19.17, 20.91, 10.67, 15.90, 9.32, 21.16, 23.44, 21.40 and 8.99±0.2 2Θ angles, most preferably at 19.17, 20.91, 10.67, 15.90, 9.32, 21.16, 23.44, 21.40, 8.99 and 15.00±0.2 2Θ angles, particularly 19.17, 20.91, 10.67, 15.90, 9.32, 21.16, 23.44, 21.40, 8.99, 15.00 and 20.64±0.2 2Θ angles.

In one embodiment, the crystalline LNT form D comprises X-ray powder diffraction reflections, based on a measurement using CuKα radiation, at 19.17±0.1 2Θ angle, preferably at 19.17 and 20.91±0.1 2Θ angles, more preferably at 19.17, 20.91 and 10.67±0.1 2Θ angles, yet more preferably at 19.17, 20.91, 10.67 and 15.90±0.1 2Θ angles, even more preferably at 19.17, 20.91, 10.67, 15.90 and 9.32±0.1 2Θ angles, even more preferably at 19.17, 20.91, 10.67, 15.90, 9.32 and 21.16±0.1 2Θ angles, even more preferably at 19.17, 20.91, 10.67, 15.90, 9.32, 21.16 and 23.44±0.1 2Θ angles, even more preferably at 19.17, 20.91, 10.67, 15.90, 9.32, 21.16, 23.44 and 21.40±0.1 2Θ angles, even more preferably at 19.17, 20.91, 10.67, 15.90, 9.32, 21.16, 23.44, 21.40 and 8.99±0.1 2Θ angles, most preferably at 19.17, 20.91, 10.67, 15.90, 9.32, 21.16, 23.44, 21.40, 8.99 and 15.00±0.1 2Θ angles, particularly 19.17, 20.91, 10.67, 15.90, 9.32, 21.16, 23.44, 21.40, 8.99, 15.00 and 20.64±0.1 2Θ angles.

Figure 4:
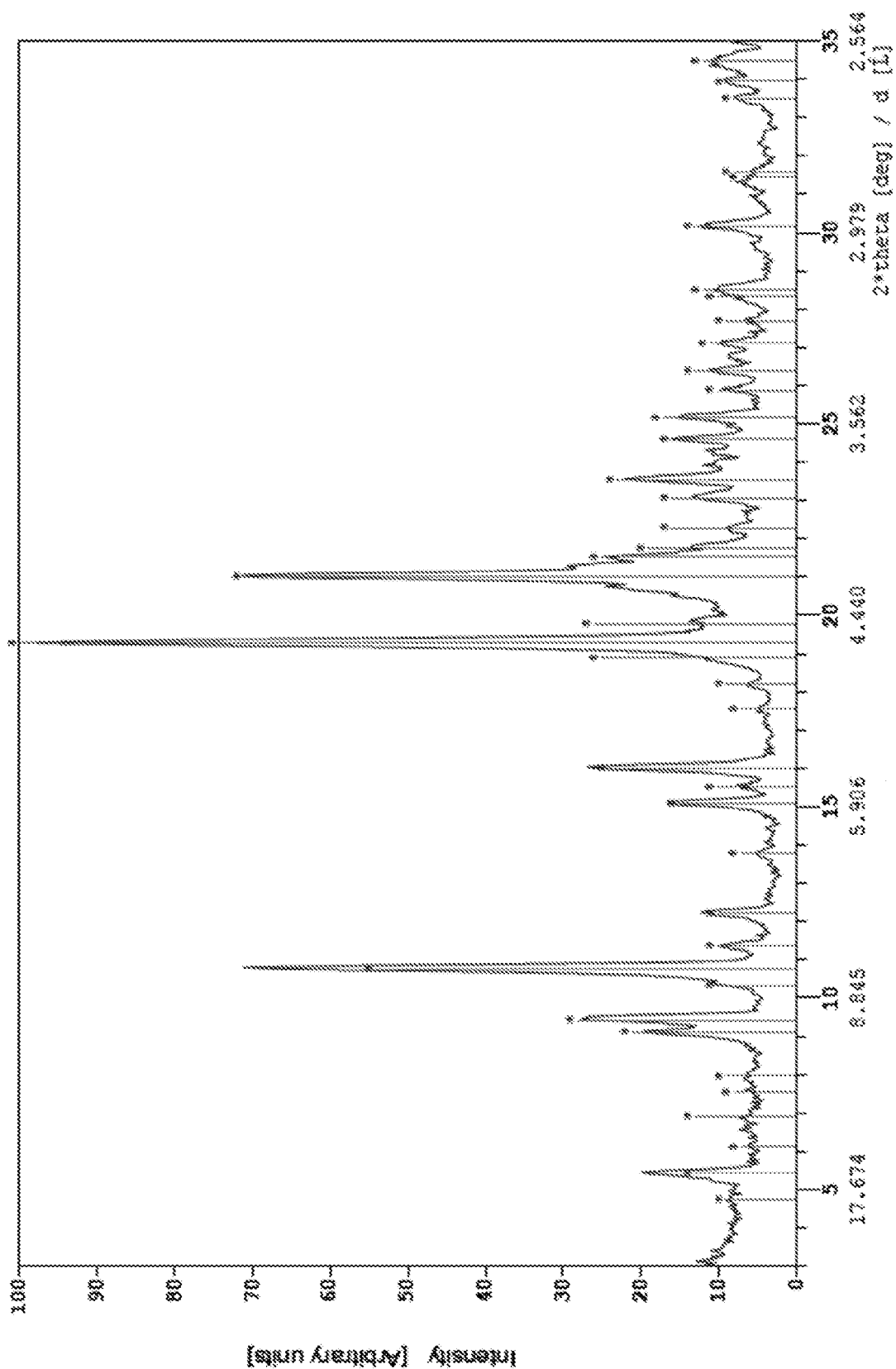
FIG. 4 shows the X-ray powder diffraction pattern of the crystalline LNT form D.

In other embodiment, the crystalline LNT form D has an X-ray powder diffraction diagram as shown in FIG. 4.

List of peaks of the XRPD pattern of the crystalline LNT form D is reported in Table 4.

TABLE 4

| 2Θ | rel. intensity |
|---|---|
| 5.31 | 14 |
| 8.99 | 15 |
| 9.32 | 24 |
| 10.28 | 6 |
| 10.67 | 70 |
| 11.24 | 6 |
| 12.11 | 9 |
| 13.68 | 3 |
| 15.00 | 15 |
| 15.40 | 3 |
| 15.90 | 25 |
| 17.44 | 2 |
| 18.07 | 4 |
| 18.72 | 7 |
| 19.17 | 100 |
| 19.73 | 10 |
| 20.40 | 10 |
| 20.64 | 15 |
| 20.91 | 72 |
| 21.16 | 20 |
| 21.40 | 16 |
| 21.66 | 9 |
| 22.12 | 6 |
| 22.97 | 11 |
| 23.44 | 20 |
| 24.16 | 8 |
| 24.48 | 14 |
| 25.04 | 13 |
| 25.78 | 7 |
| 26.27 | 9 |
| 26.68 | 6 |
| 26.96 | 8 |
| 27.60 | 4 |
| 28.36 | 8 |
| 29.52 | 3 |
| 30.08 | 9 |
| 30.76 | 3 |
| 31.20 | 5 |
| 31.48 | 3 |
| 33.40 | 6 |
| 33.799 | 7 |
| 34.36 | 9 |
| 22.12 | 6 |

LNT crystalline form D has a capillary melting point 249-251° C. The air dried sample has a water content of about 2.7 wt %.

LNT crystalline form D can be typically obtained form C under forced drying conditions so that form C undergoes dehydration while the crystalline phase changes. For example the vacuum drying requires several days to convert form C to form D. At atmospheric pressure, if the temperature is high, shorter time may be sufficient.

The powder X-ray diffraction patterns of the crystalline LNT forms A to D of this invention are different from each other as the notable differences show in their diffractogram.

Each of the LNT crystalline forms A, B, C and D can be considered as an anomeric mixture of α- and β-anomers or even a pure form of one of the anomers.

Preferably, each of the crystalline LNT forms A, B, C and D of this invention is substantially pure. The expression "substantially pure" preferably means that the crystalline LNT polymorph contains less than 10 w/w % of impurity, preferably less than 5 w/w % of impurity, more preferably less than 1 w/w % of impurity, most preferably less than 0.5 w/w % of impurity, in particular less than 0.1 w/w % of impurity, wherein "impurity" refers to any physical entity different from the crystalline LNT form in question, such as an amorphous LNT, different LNT polymorph(s) or form(s), unreacted intermediate(s) remained from the synthesis of LNT, by-product(s), degradation product(s), inorganic salt(s) and/or other contaminants different from organic solvent(s) and/or water.

Each of the crystalline LNT forms A, B, C and D according to this invention is suitable for pharmaceutical and nutritional use. In this regard, LNT, alone or in combination with other N-acetyllactosamine and/or fucose and/or sialic acid containing human milk oligosaccharides, is particularly effective in the education and/or maturation of the immune system of neonatal infants, and have preventive effect against secondary infections following viral infections such as influenza. The use of LNT as prebiotic enhances the beneficial effects and efficiency of probiotics, such as *Lactobacillus* and *Bifidobacterium* species, in promoting the development of an early bifidogenic intestinal microbiota in infants, in reducing the risk of development or allergy and/or asthma in infants, in preventing and treating pathogenic infections in such as diarrhoea in infants.

Also in accordance with this invention, a pharmaceutical composition is provided comprising the crystalline LNT form A, B, C or D of the invention, or their combination, as an active ingredient and one or more pharmaceutically acceptable carriers such as additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.). Suitable carriers are described in the most recent edition of Remington's Pharmaceutical Sciences, a standard reference text in the field. The dosage form for administration includes, for example, tablets, powders, granules, pills, suspensions, emulsions, infusions, capsules, syrups, injections, liquids, elixirs, extracts and tincture.

Also in accordance with this invention, the crystalline LNT form A, B, C or D of the invention, or their combination, can be used for the preparation of pharmaceutical compositions. Pharmaceutical compositions can be manufactured in a conventional manner, e.g. as described in the most recent edition of Remington's Pharmaceutical Sciences, a standard reference text in the field.

Further in accordance with this invention, a nutritional formulation (such as food, drink or feed) is provided comprising the crystalline LNT form A, B, C or D of this invention, or their combination. The nutritional formulation can also contain edible micronutrients, vitamins and minerals as well. The amounts of such ingredient can vary depending on whether the formulation is intended for use with normal, healthy infants, children, adults or subjects having specialized needs (e.g. suffering from metabolic disorders). Micronutrients include for example edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolysed cornstarch, etc.) and proteins from casein, soy-bean, whey or skim milk, or hydrolysates of these proteins, but protein from other source (either intact or hydrolysed) may be used as well. Vitamins may be chosen from the group consisting of vitamin A, B1, B2, B5, B6, B12, C, D, E, H, K, folic acid, inositol and nicotinic acid. The nutritional formulation can also contain the following minerals and trace elements: Ca, P, K, Na, Cl, Mg, Mn, Fe, Cu, Zn, Se, Cr or I.

In a preferred embodiment, the nutritional formulation is an infant formula, i.e. a foodstuff intended for use by infants during the first 4-6 months of life and satisfying, by itself, the nutritional requirements of infants. It can contain one or more probiotic *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet. The infant formula preferably contains the crystalline LNT form A, B, C or D of the invention, or their combination, in a total amount of 0.1-3.0 g/100 g of formula.

In another preferred embodiment, the nutritional formulation can be a food supplement containing the crystalline LNT form A, B, C or D of the invention, or their combination. The food supplement can also contain one or more probiotics in an amount sufficient to achieve the desired effect in an individual, preferably in children and adults. The food supplement can also contain vitamins, minerals, trace elements and other micronutrients as well. The food supplement may be for example in the form of tablets, capsules, pastilles or a liquid. The supplement can also contain conventional additives, such as binders, coatings, emulsifiers, solubilising agents, encapsulating agents, film forming agents, adsorbents, carriers, fillers, dispersing agents, wetting agents, jellifying agents, gel forming agents, etc. The daily dose of LNT typically ranges from 0.1 to 3.0 g.

According to a more preferred embodiment, the food supplement is a digestive health functional food as the administration of LNT provides a beneficial effect on digestive health. Digestive health functional food is a processed food used with intention enhance and preserve digestive health by crystalline LNT according to the present invention as physiologically functional ingredient or component in forms of tablet, capsule, powder, etc. Different terms such as dietary supplement, nutraceutical, designed food, health product may also be used to refer to functional food.

In a further embodiment, the crystalline LNT form A, B, C or D of the invention, or their combination, is used for the preparation of nutritional formulations, such as foods, drinks and feeds, preferably infant formulas, food supplements and digestive health functional food. The nutritional formulations can be prepared in a conventional manner. For example, it can be prepared by admixing micronutrient components in appropriate proportions, and then adding vitamins and minerals while avoiding thermal degradation or decomposition of heat sensitive vitamins by adding them after homogenization. Lipophilic vitamins can be dissolved in a fat source before mixing. A liquid mixture is formed using water, whose temperature is preferably about 50-80° C. to help dissolution or dispersal of the ingredients. The crystalline LNT form A, B, C or D, or their combination, can be suitably added at this stage. The resulting mixture is then homogenized by flash heating to about 80-150° C. by means of steam injection, heat exchanger or autoclave. This thermal treatment also reduces significantly the bacterial load. The hot mixture is then cooled rapidly to about 60-80° C. If needed, further homogenization can be carried out at this temperature under high pressure of about 2-30 MPa. After cooling, heat sensitive constituents can be added, and the pH and the solids content can be conveniently adjusted. The resulting mixture is then dried in a conventional manner, such as by spray drying or freeze drying to powder. Probiotics can be added at this point by dry-mixing.

Other features of the invention will become apparent in the course of the following descriptions of exemplary embodiments which are given for illustration of the invention and are not to be limiting thereof.

EXAMPLES

XRPD investigation of the collected crystals was conducted with a Philips PW 1830/PW1050 instrument in transmission geometry, using CuKα radiation made monochromatic by means of a graphite monochromator. D-spacings were calculated from the 2Θ values, based on a wavelength of 1.54186 Å. As a general rule the 2Θ values have an error rate of ±0.2. The recorded XRPD diagrams are shown in FIGS. 1 to 4.

Form A

LNT (1.0 g) was dissolved in water (5 ml). Abs. EtOH (4.5 ml) was added at room temperature, resulting in a clear solution. Crystals were obtained after stirring the solution for 18 hours at room temperature. The crystals were filtered off, washed with approx. 3 ml abs. EtOH and dried. Mp.: 226-228° C.

Form B

An aqueous solution containing LNT (17.5 g) was concentrated to Brix 48° and heated to 80° C. for full dissolution, then allowed to slowly cod down to room temperature. After 18 hours, a thick suspension was obtained which was diluted with water (5 ml) to afford a nicely stirrable slurry. After 1 hour of stirring at room temperature the crystals were filtered off, and the wet cake was dried on air for 9 days to get a white solid (14.6 g).

Form C

I) An aqueous solution containing LNT (25 g) was concentrated to Brix 37°, heated to 50° C. and methanol (50 ml) was added to the hot solution. Seeding crystal of form B (100 mg) and a second portion of MeOH (50 ml) were added. After 45 minutes a third portion of MeOH (50 ml) was added. The obtained suspension was allowed to cool down and stirred at 25° C. for 2 hours. The solid was filtered off, washed with 50 ml of MeOH and dried in vacuum oven for 17 hours at 60° C. and 30 mbar (15.5 g). Mp.: 252-255° C.

II) LNT (9.7 g) dissolved in water (33 ml)) was heated to 60° C. Methanol (66 ml) was slowly added over 35 min. The solution was stirred at 60° C. and after 15 min spontaneous nucleation occurred. The suspension was stirred for 2 hours at 60° C. before being slowly cooled to 40° C. over 1.5 hours. The suspension was further stirred at 40° C. for 14 hours. The suspension was then allowed to cool to 25° C. and further stirred at this temperature for 2 hours. Crystals were filtered off and washed with 10 ml of methanol. Wet crystals were dried at 50° C. and 50 mbar for 21 hours, giving a crystaline material having a water content of 9.4%, the XRPD pattern of which is identical with that of the sample obtained above.

III) An aqueous solution containing LNT (34 g) was concentrated to brix 24°. At 35° C. a first portion of MeOH (150 ml) was added. The solution was seeded with polymorph C. Further MeOH (150 ml) was added in 25 ml portions over a period of 1 hour. The suspension was stirred at 35° C. for 3 hours, then heated up to 55° C., stirred at 55° C. for 6 hours, then cooled down to 35° C. and stirred at 35° C. for 4 hours. The solid was filtered off, washed with 60 ml of MeOH and dried in vacuum oven at 60° C. and 50 mbar for 5 hours to afford a crystalline material (29 g), which was identical, according to XRPD, with the sample obtained above, and had a water content of 9.1% (by Karl-Fisher titration).

Form D

1) An aqueous solution containing LNT (32 g) was concentrated to Brix 24°, heated to 35° C. and MeOH (150 ml) was added to the warm solution. Seeding crystal form C (300 mg) and a second portion of MeOH (150 ml) was added in 25 ml portions over a period of 1 hour. The suspension was stirred at 35° C. for 3 hours, at 55° C. for 6 hours, then was allowed to cool down to 30° C. and stirred for 4 hours at this temperature. The solid was filtered off, washed with 50 ml of MeOH and dried in oven at 70° C. for 22 hours at atmospheric pressure (28.6 g). Mp.: 249-251° C.

II) LNT form C was further dried in a vacuum oven for 20 days at 60° C. and 20 mbar to give form D according to XRPD.

The invention claimed is:

1. A crystalline substantially pure form of LNT having an X-ray powder diffraction pattern characterized by peaks at two theta angle of 19.17±0.2, 20.91±0.2 and 10.67±0.2, based on a measurement using CuKα radiation.

2. A pharmaceutical composition comprising the crystalline substantially pure form of LNT of claim 1 and one or more pharmaceutically acceptable carriers.

3. The crystalline substantially pure form of LNnT of claim 1, wherein the X-ray powder diffraction pattern is characterized by peaks at two theta angles of 19.17±0.2, 20.91±0.2, 10.67±0.2 and 15.90±0.2, based on a measurement using CuKα radiation.

4. The crystalline substantially pure form of LNnT of claim 1, wherein the crystalline form of LNnT has an X-ray powder diffraction diagram as shown in FIG. 4.

5. The crystalline form of LNnT of claim 1, wherein the crystalline substantially pure form of LNnT has a capillary melting point from 249 to 251° C.

* * * * *